United States Patent [19]

Zwiener

[11] 4,040,750
[45] Aug. 9, 1977

[54] REAL TIME REFLECTOMETER

[75] Inventor: James M. Zwiener, Madison, Ala.

[73] Assignee: The United States of America as represented by the Administrator of the National Aeronautics and Space Administration, Washington, D.C.

[21] Appl. No.: 691,256

[22] Filed: May 28, 1976

[51] Int. Cl.² .......................................... G01N 21/48
[52] U.S. Cl. ................................................. 356/212
[58] Field of Search ....................... 356/209, 211, 212

[56] References Cited

U.S. PATENT DOCUMENTS

| 2,808,755 | 10/1957 | Millen | 356/212 |
| 3,499,716 | 3/1970 | Bennett | 356/209 |
| 3,960,077 | 6/1976 | Aylett | 356/212 |

OTHER PUBLICATIONS

Onton et al., "High-Sensitivity Reflectance Measuring Device," *IBM Technical Disclosure Bulletin*, vol. 14, No. 6 (Nov. 1971) pp. 1868-1869.

*Primary Examiner*—John K. Corbin
*Assistant Examiner*—Richard A. Rosenberger
*Attorney, Agent, or Firm*—L. D. Wofford, Jr.; George J. Porter; John R. Manning

[57] ABSTRACT

A real time reflectometer with the particular utility of measuring fairly rapid (transient) changes in the specular reflectance of a sample which is continuously exposed to a perturbing environment containing a fixed radiation source, a fixed detector, a uniformly rotating sample wheel and a uniformly rotating optical wheel. The plane of rotation of the sample wheel and the optical wheel are normal to one another, and the gear drives of both wheels are interconnected and are driven by a single drive motor thereby insuring the alignment of the mirrors contained on the optical wheel with the sample present on the sample wheel. The radiation source generates light directed toward the uniformly rotating sample wheel, said sample wheel containing a test sample and an aperture. Light reflected off the test sample is also reflected from the optical wheel and directed toward the detector. The reflectance value of the reflected light is compared to that of a reference signal established by light passing through the aperture, reflected from the optical wheel and directed toward the detector. Except for the fact that the reference and the sample will have different reflectance values, the optics and the optical path length for the sample reflectance and the reference signals are identical.

7 Claims, 7 Drawing Figures

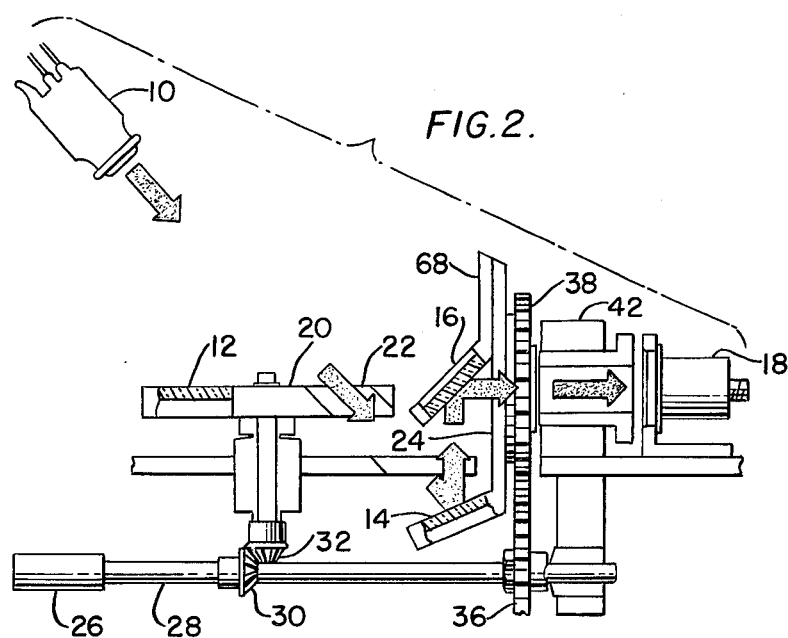
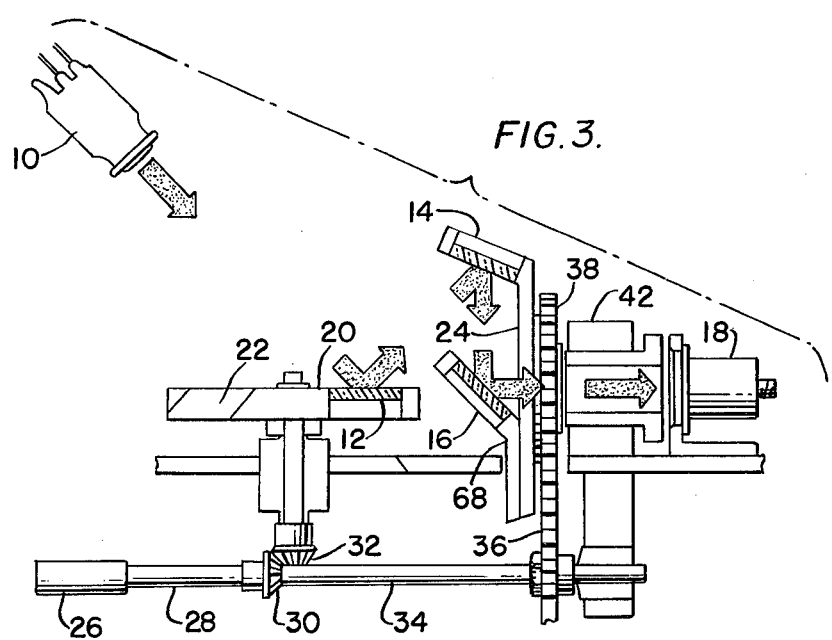

REAL TIME REFLECTOMETER

ORIGIN OF THE INVENTION

The invention described herein was made by an employee of the U.S. Government and may be manufactured and used by or for the Government of the United States of America for governmental purposes without the payment of any royalties thereon or therefor.

FIELD OF THE INVENTION

The present invention relates to reflectometers used to measure transient reflectance values of a sample which is exposed to a perturbing environment such as a rocket engine or control thruster firing which can change optical properties rapidly as effluents, such as hydrocarbons or silicates, are deposited on various surfaces.

BACKGROUND OF THE INVENTION

Many techniques and devices have been recently developed in the field of optics for measuring the specular reflectance of a particular sample. When deciding which of these techniques or devices would be the most appropriate for a particular surface, several factors such as the approximate value of the reflectance, whether this reflectance is to be measured in the visible, infrared or vacuum ultra-violet (VUV) spectrum, and what level of accuracy is desired must be considered.

One such technique is discussed in the Journal of the Optical Society of America, Volume 50, No. 1, Page 1, January, 1960 by H. E. Bennett and W. F. Koehler and in U.S. Pat. No. 3,499,716 to Bennett. This method of measuring reflectance utilizes the so-called V-W or Strong-type reflectometer. This device uses a revolving mirror and a movable sample so that the source beam first strikes the mirror in a reference position to obtain a hundred percent signal and then the mirror is moved to a reflectance position and the sample is inserted in the light beam in such a manner to allow the beam to be twice reflected off the sample, providing a measurement of the square of reflectance. While the optical path length of the beam of light is unchanged, it should be noted that to reduce problems of detector surface sensitivity variations with misalignments, an integrating sphere is placed in front of the detector so that its surface is always uniformly illuminated even with sample misalignment. However, one disadvantage of this approach is the limited wavelength usefulness of the Bennett device in conjunction with these integrating spheres, thereby allowing reflectance measurements to be made only in the visible and infrared regions. This is due to the excessive number of reflectances which must take place and the use of the integrating sphere. Furthermore, the V-W measurement technique does not lend itself toward taking measurements of transient reflectance effects due to the relative long time duration between the measurement of the reference and reflectance signals.

An apparatus for the measurement of vacuum ultra-violet (greater than 500A) optical properties is reported by Madden and Canfield in the Journal of the Optical Society of America, Volume 51, No. 8, 1961, Page 838. This device employs the single beam reflectance measurement technique of utilizing a movable detector and sample. To obtain the reference reading, the sample is removed from its position and the detector is rotated to a position for measuring the unperturbed beam. Of special importance is the fact that this technique permits measurement of the angular dependance of reflection and polarization effects (with the addition of a polarizer at the source). Furthermore, the optical path length is identical between the detector and source at both reflectance and reference positions; therefore, source beam divergence or intensity is the same on the detector at both positions. In addition, this technique can be used over a broad range of wavelengths from the X-ray to far infra-red, limited only by source and detector problems. However, one such problem area with this technique is the positioning of the detector accurately so that the source beam falls on the same portion of the detector surface at all times. This is an acute problem since the detector is in motion and a 1° misalignment of the mirror in angular positioning would represent twice the area in reflectance measurements at the detector. A further problem relates to the stability of the light source. Since several minutes, if not longer, will elapse between reflectance and reference measurements, a shift in the source output will directly affect the signal, causing an error in the reflectance readings.

A classical solution to several of the problems associated with the single beam technique is to utilize what is called the dual beam reflectance measuring technique. This method is identical to the single beam procedure with the addition of an oscillating mirror and a detector reference. In this particular method, the oscillating mirror focuses the light from a source or monochrometer, first onto the detector reference, and then onto the sample or first detector. This system provides a constant monitoring of the light source output, permitting corrections for drift of the source between the reflectance and the reference signal measurements with the first detector. However, problems arise in alignment of the oscillating mirror and the sample as mentioned in the single beam measurements. Additionally, if the reference detects drifts or changes in sensitivity, this will be interpreted as a change in light source output, and an error in reflectance will occur.

Additionally, several reflectometers utilize a reference sample as a reference reading for comparison to the reflectance reading. Since these samples are subjected to the perturbing atmosphere, they can be contaminated thereby causing an error in the true reflectance values.

A review of the prior art devices, therefore, reveals that no device has been developed which both operates in the infra-red, visible, and vacuum ultra-violet regions and also contains a fixed source and detector having identical path lengths, thus eliminating misalignment errors. Furthermore, none of the references is capable of measuring fairly rapid changes in the reflectance of a sample which is exposed continuously to a perturbing environment.

SUMMARY OF THE INVENTION

It is therefore an object of the present invention to overcome the defects of the prior art as disclosed above.

Another object of the present invention is to produce a reflectometer which is designed to measure fairly rapid changes in the reflectance of a sample.

A still further object of the present invention is to produce a reflectometer which can measure reflectance in the infrared, visible and vacuum ultra-violet regions.

Yet another object of the present invention is to produce a reflectometer which utilizes common optics and identical optical paths.

Another object of the present invention is to produce a reflectometer which utilizes a fixed detector and a fixed source.

A still further object of the present invention is to produce a reflectometer which utilizes uniformly rotating sample and optical wheels.

Yet another object of the present invention is to produce a reflectometer which permits bulky or awkward light sources and detector systems to be readily attached and aligned while still providing accurate reflectance measurements during the time the entire device is exposed to severe environments.

Still another object of the present invention is to produce a reflectometer which can measure both specular and scatter (slightly off specular) components of the reflectance of a sample.

These and other objects of the present invention are accomplished by a real time reflectometer which can measure both specular reflectance (where the angle of incidence equals the angle of reflectance) along with off-specular components. This reflectometer also measures rapidly changing values in reflectance of a sample by comparing the measurements of a reflected signal with that of a reference signal made within fractions of a second of one another, while protecting against misalignment problems between a sample wheel, optical wheel, source and detector.

The present reflectometer contains a uniformly rotating sample wheel provided with a sample and an aperture through which radient energy may directly pass. A uniformly rotating optical wheel (rotating in a plane perpendicular to the plane of rotation of the sample wheel) whose drive gears are interconnected with the drive gears of the sample wheel is provided with two precisely aligned mirrors so that light striking the sample or passing through the aperture is directed into a detector. Since the sample is only rotating along the circumference of a small circle and is constantly facing in the same direction, the sample would be continuously exposed to the perturbing environment. Furthermore, since common optics are used and the optical path lengths of the reflectance and reference measurements are identical, the absolute values of the reflectance are of a more precise nature. Additionally, because there is a maximum of only three reflectances, the optical properties of a sample in a VUV environment can be investigated.

BRIEF DESCRIPTION OF THE DRAWINGS

The above and additional objects and advantages inherent in the present invention will become more apparent by reference to the description of an illustrated embodiment drawing thereof in which:

FIG. 2 is a schematic diagram of the reflectometer illustrating the reference signal measurement position;

FIG. 3 is a schematic diagram of the reflectometer illustrating the reflectance measurement position;

DETAILED DESCRIPTION OF THE PREFERRED EMBODIMENT

Figure 1:
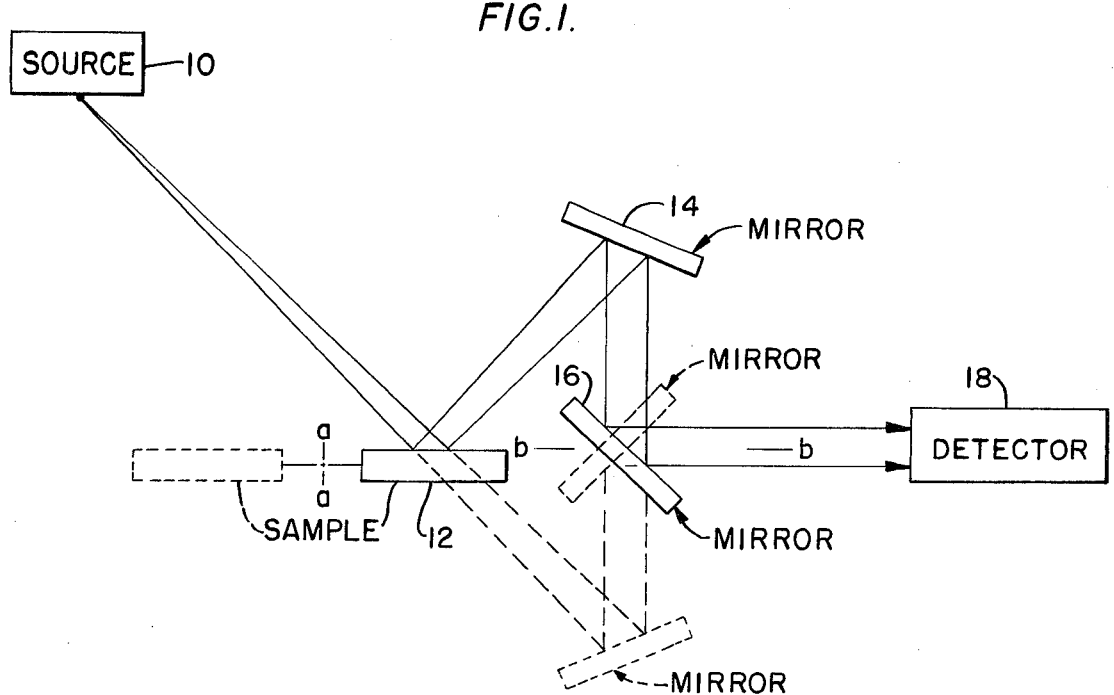
FIG. 1 is a schematic diagram illustrating one optical system of the reflectometer.

Referring to the drawings, FIG. 1 shows a schematic diagram which illustrates one optical system of the reflectometer of the present invention. The solid lines in FIG. 1 indicate the position of a circular sample wheel, a circular optical wheel and the radient energy path when the reflectometer is in the reflectance measurement position. This position is also shown in FIG. 3. Source 10 provides a continuous supply of radiation, which in the reflectance position, is reflected off of sample 12, plane mirrors 14 and 16 and into the detector 18.

The sample wheel and optical wheel positioning, in addition to the path of radient energy in the reference measurement position, are denoted by the dashed lines in FIG. 1, and are also shown in FIG. 2. This position is obtained by simultaneously rotating the sample wheel 20 about axis $a-a$ while mirrors 14 and 16, mounted upon optical wheel 24, are rotated about axis $b-b$, both wheels being rotated 180° between the two operating modes.

In the reference measurement position, the energy generated by source 10 passes through aperture 22 on the sample wheel 20 and is then reflected off of mirrors 14 and 16 and onto detector 18. This signal is compared to the reflectance measurement to determine the reflectance of the sample while it is being subjected to a perturbing environment. Additionally, the sample 12 is merely rotated along the circumference of a small circle and therefore the sample 12 is always in a direct line of sight of its environment. Furthermore, the optical path lengths for both the reflectance and reference measurements is identical, and since the source 10 and the detector 18 can remain stable, the problems associated with the misalignment of the source and the detector in the single beam reflectometer are avoided.

Figure 4:
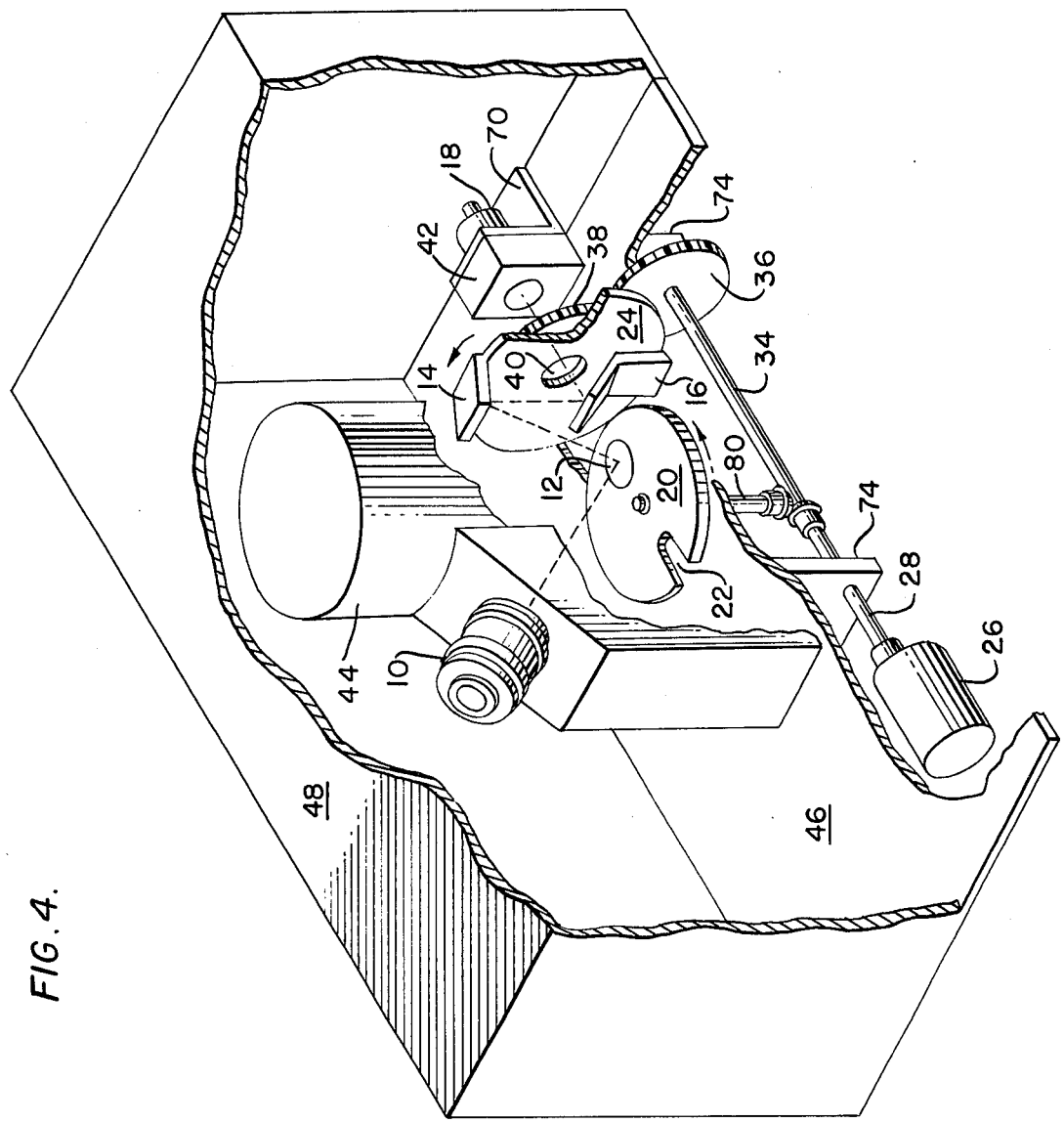
FIG. 4 is a perspective schematic drawing of the entire reflectometer system.

FIG. 4 shows a simplified cut-away schematic of the interior of the real time reflectometer system when it is in the reflectance signal measurement position. A variable speed drive motor 26 adjustable to different frequency or measurement rates (such as between 30 and 60 r.p.m.) is connected through shaft 28 to bevel gears 30 and 32 and shaft 50, allowing the rotational movement of this shaft 28 to be translated to the rotational movement of the sample wheel 20. The drive motor 26 simultaneously rotates the circular optical wheel 24 through the rotation of shaft 34 and toothed drive gears 36 and 38. The toothed drive gear 38 is directly affixed to the posterior of optical wheel 24 thereby ensuring that the optical wheel will rotate properly. The optical wheel 24 also contains an aperture 40, aligned with detector 18 and mirrors 14 and 16, thereby allowing the radiant energy to pass directly into the detector 18. A bearing block 74 is provided at the end of shaft 28 to stabilize the operation of same. Bearing block 42 is provided to stabilize optical wheel 24 and gear 38. It should be noted that both sets of drive gears 30, 32 and 36, 38 are in a one-to-one ratio enabling the sample wheel 20 and the optical wheel 24 to maintain alignment while rotating. In addition, although FIG. 4 shows the sample wheel 20 and optical wheel 24 being rotated in a counter-clockwise motion, it can be appreciated that this need not be the case and that if both the sample wheel 20 and optical wheel 24 were rotated in the opposite direction, the present invention would be equally operable.

Due to the symmetrical optics involved in this invention, it should be noted that the detector 18 and the source 10 can be switched in location. Furthermore, a spectrometer arrangement could be located at the position of the detector 18 in order for spectral reflectance measurements over large ranges of wavelength to be made. In fact, several wavelengths could be monitored simultaneously by positioning several detectors inside the spectrometer at the appropriate light dispersion locations.

Figure 5:
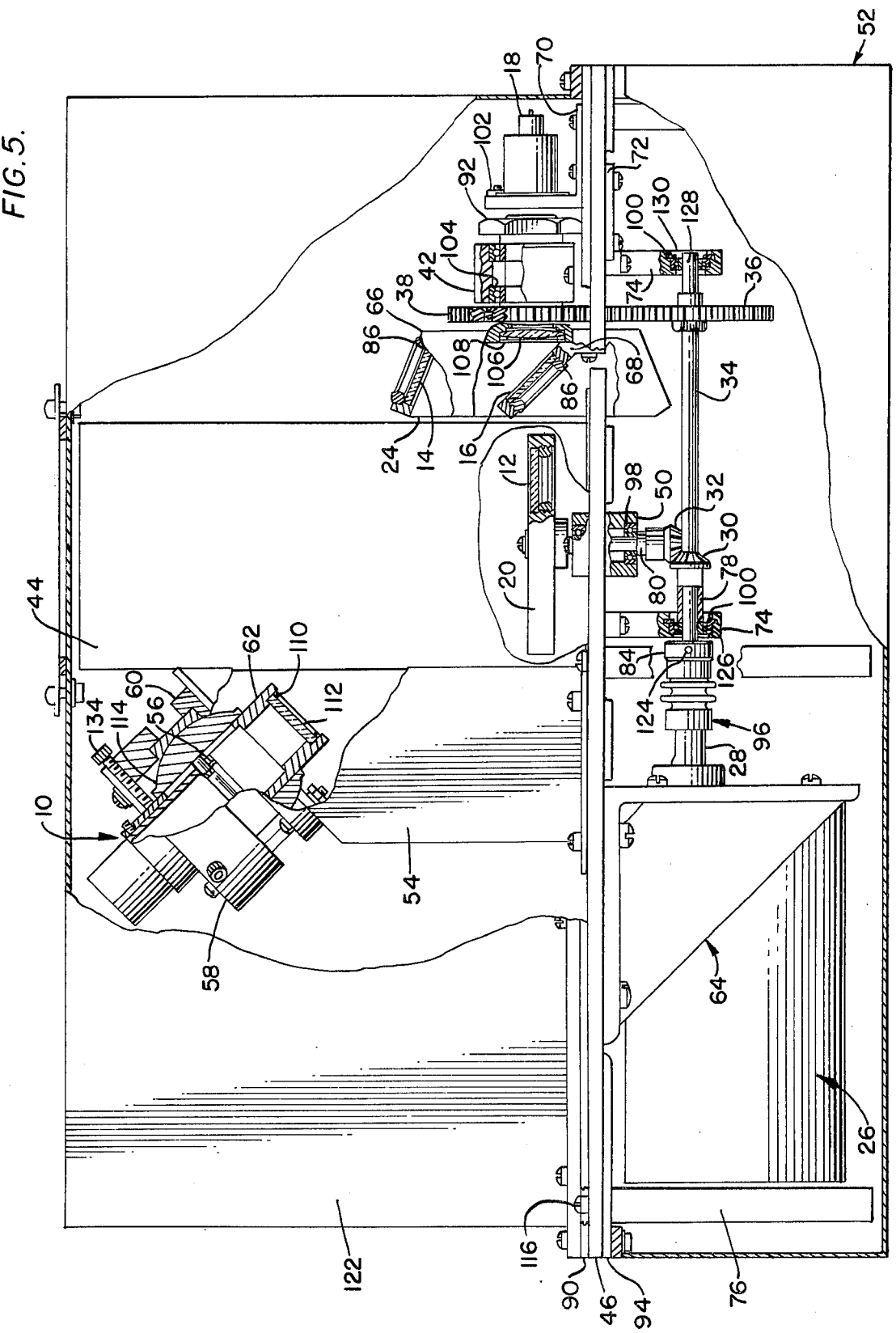
FIG. 5 is a partially sectioned side view of the reflectometer.
Figure 6:
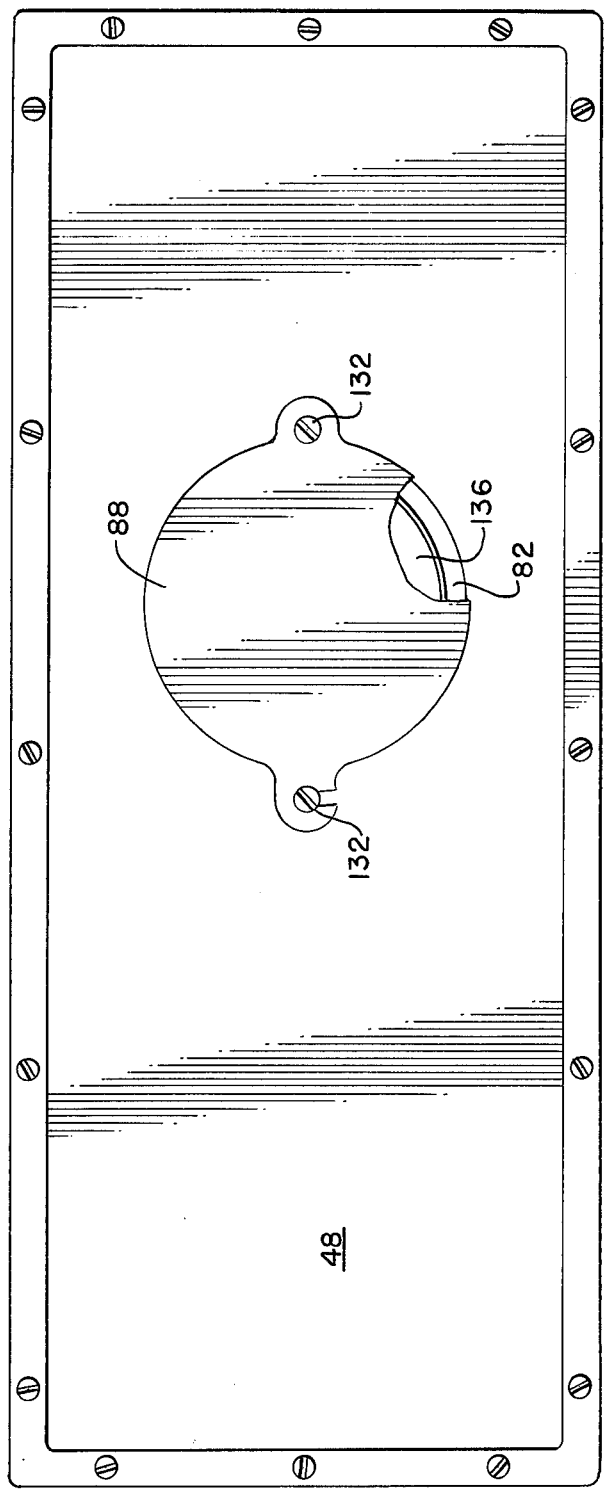
FIG. 6 is a top view of the reflectometer.

Referring now to FIGS. 5 and 6, which are detailed drawings of one embodiment of the present invention, a substantially rectangular mounting plate 46 is provided for firmly supporting the source 10, the drive motor 26, the optical wheel 24, the detector 18 and various interconnections therebetween. A plurality of support legs 76 is connected to the mounting plate 46 by a number of screws 116 to adequately stabilize the real time reflectometer when cover 52 is removed for adjustments. The drive motor 26 is supported to the bottom surface of the mounting plate 46 by a triangularly-shaped motor mount 64. The substantially circular sample wheel 20 containing the aperture 22 and sample 12 is rotatably connected to the drive mechanism of the drive motor (described hereinbelow in further detail) through the shaft in bearing block 50 and bevel gears 30 and 32, allowing the sample wheel to rotate above the mounting plate 46 at approximately the midpoint of same.

Figure 7:
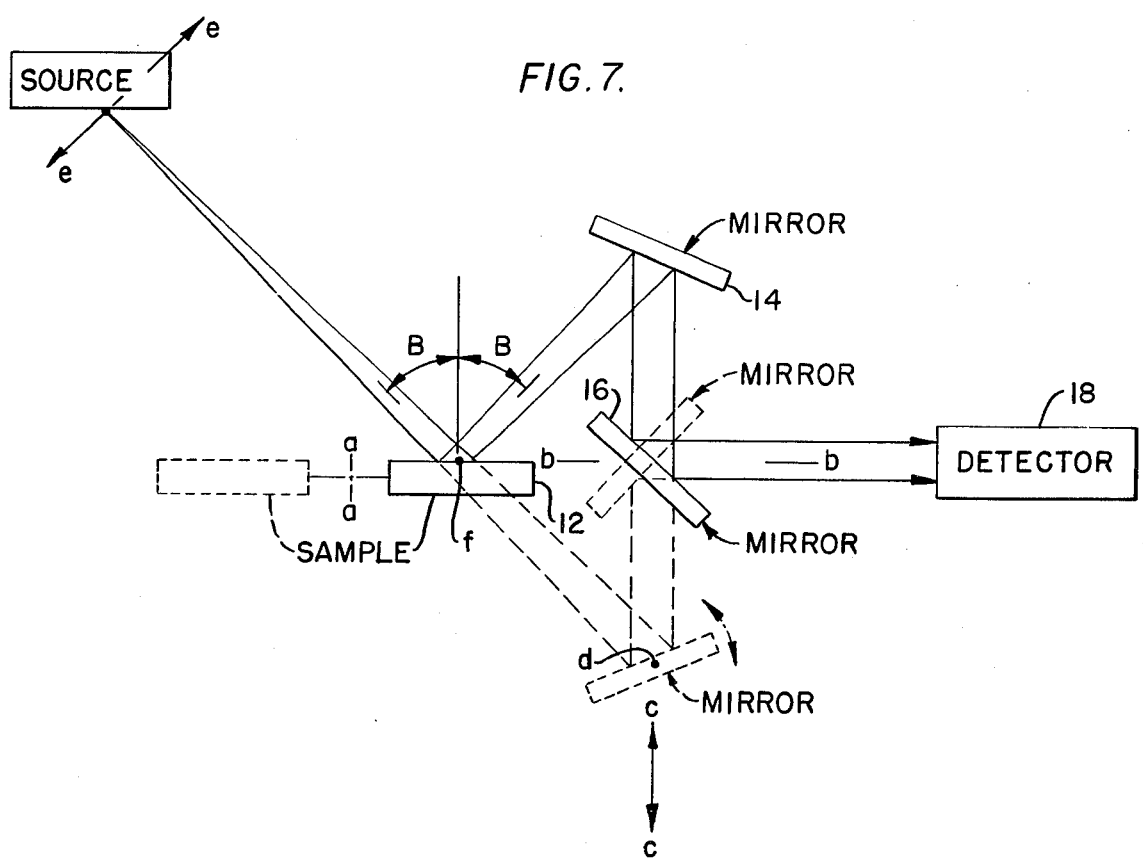
FIG. 7 is a schematic diagram illustrating the optical system of another embodiment of the present invention.

The optical wheel 24 includes a mirror cone 66 for the protection and mounting of mirrors 14 and 16. Mirror 14 is directly affixed to the inside surface of the cone 66 by a mirror retainer 86 directly mounted upon the surface of wheel 24. Mirror 16 is affixed to mirror mount 68 by a retainer 86, the whole of which is attached to cone 66. It is important to note that mirror 16 must be positioned at an angle of 45° with respect to the horizontal to ensure that the reflected radient energy is properly transmitted to the detector 18. The exact angle and position of mirror 14 is determined by the angle of incidence and reflectance of the light source (FIG. 7, B). As the angle of incidence (measured to a normal or vertical at 12) decreases, mirror 14 moves farther away from mirror 16 (in order to intercept reflected light) and its angle to the horizontal decreases in order to reflect light onto mirror 16 and then to detector 18.

The mirror cone 66 and the optical wheel 24 are mounted substantially above the mounting plate 46, but a portion does lie below the plate 46 and therefore an aperture is provided therein to allow the mirror cone to freely rotate. It is important to note that the plane of rotation of the optical wheel 24 must be perpendicular to the plane of rotation of the sample wheel 20; and rotation axis b—b (FIG. 1) lies in the surface plane of mirror 12.

Posterior to the mirror cone 66 is the detector 18 mounted directly upon the upper surface of the mounting plate 46 using detector mount 70, strap 72 and clamp cleat 102. This detector may be an NO gas filled ion chamber, or as previously mentioned, can be a spectrometer. In order to increase the energy reaching the detector 18, a lens 106 is provided within an aperture directly in front of the detector 18. If specular reflectance data is required in the VUV range (above 112.0nm), an MgF$_2$ type lens can be inserted instead of lens 106 within a split retaining ring 108 contained in aperture 40. If specular reflectance data is to be obtained in the wavelength region (200.0nm to 2500nm) then an integrating sphere and appropriate detectors (such as a Photomultipler tube and PbS cell) can be used to replace detector 18 and its associated hardware. This sphere reduces the problem of detector surface sensitivity variations with misalignments by always uniformly illuminating the surface of the detector.

Between optical wheel 24 and detector 18, a bearing block 42 containing bearing 104, and connected to a hexagonal nut 92, is provided for ensuring a smooth rotation of the optical wheel. The mirror cone 66 contains a rotating shaft (not shown) attached to the intereior of this bearing block 42 for this purpose. The rotating shaft is hollow, and nut 92 and bearing block 42 contain a hole therein for allowing the reflected radient energy to pass into detector 18.

A housing 54 is provided above the mounting plate 46 between the drive motor 26 and the sample wheel 20 for supporting the radiation source 10. Although many types of radiation sources may be utilized, in this particular embodiment of the design a hydrogen DC discharge lamp was utilized with an MgF$_2$ window 112 for collimating the radient energy, said lamp retained by a lens holder 62 and a split retaining ring 110. For ease in installing and changing the position of the source 10, a front mount 60, rear mount 58, spherical bearing 114 and set screw 134 are provided.

As indicated hereinabove, the sample wheel 20 and the optical wheel 24 are simultaneously and precisely rotated to prevent misalignment problems and thus insure that a true value of reflectance will be obtained. This drive mechanism contains a rotating cylindrical shaft 28 connected to a coupling 96 and a coupling adapter 84 having a set screw 124. Adjacent to the coupling adapter 84 is a bearing block 74 containing bearing 126 and retaining ring 100. A shaft spacer 78 is positioned on shaft 34 in order to maintain engagement of gears 30 and 32; thereby translating the rotating motion of shaft 28 (or 34) to the sample wheel 20. Also provided for this purpose is a shaft 80, bearing housing 50 and a bearing 98 within the housing 50, Section 34 of shaft 28 allows the optical wheel 24 to rotate in synchronization with the sample wheel 20. This shaft is connected to gear 36 which meshes with gear 38. Gear 38 is directly affixed to the optical wheel 24 and therefore a rotation of gear 38 would allow the mirror combination to rotate. For stabilization effects, the end of the rotating drive shaft 128 (an extension of shaft 34) is contained in a bearing block 74 provided with a retaining ring 100 and a bearing 130.

In order to properly protect the reflectometer, a bottom rectangular cover 52 and a rectangular-shaped body cover 122 having a rectangular top cover 48 are provided to completely enclose the device. The bottom cover 52 and the body cover 122 are both affixed to the mounting plate 46, and a gasket 94 is provided around the edges of these covers to insure a proper seal. This cover 48 additionally contains a viewing port 136 which enables exposure of sample 12 to its perturbing environment, and permits an observer to view the rotating sample wheel 20. A cylindrical-shaped shield can 44 extending from the mounting plate 46 to the top of the reflectometer completely encircles the sample wheel 20 and provides light baffling, apertures, and protection of internal optics and mechanisms. The top cover 48 also contains a viewing port cover 88 and gasket 82 for completely sealing the reflectometer. This cover 88 can be inserted or removed from its position via screws 132. The cover 122 can also be constructed to contain an opening near detector 18 to allow the utilization of a bulky detector such as a spectrometer.

In operation, the entire reflectometer is introduced into a monitored perturbing environment with a sample plate suitably attached to the sample wheel 20. The viewing port cover 88 is removed and the drive motor 26 and the source 10 are activated. Radient energy is then reflected off the sample and passed to detector 18, and compared to a reference signal generated by the radient energy passing through aperture 22 and then being reflected off mirror 14 and 16 into the detector 18. In this manner, the reflectance value of the sample in a particular environment can be ascertained in only fractions of a second.

FIG. 7 shows a schematic drawing of an optical system of another embodiment of the present invention. This embodiment allows the reflectometer to measure the off specular (scatter) components of the sample, limited in angle only by the physical dimensions of the device. In practice, mirror 14 is mounted on a sliding shaft affixed to the optical wheel 24 and driven along direction $c$—$c$ by a drive gear and follower. Rotation about axis $d$ is accomplished with another gear drive system ensuring that the radient energy beam travelling from mirror 14 to mirror 16 will be maintained in the same direction as mirror 14 translates along axis $c$—$c$.

Additionally, this reflectometer can be modified to include measurements of reflectance versus angle of incidence. This measurement is accomplished by use of the embodiment described in the previous paragraph and by mounting source 10 on a pivoting arm allowing same to transcribe the arc $e$—$e$, with a center of rotation at point $f$. It should be noted that source 10 and mirror 14 must be adjusted so that the angles B are always equal to each other.

While this device has been described with particular reference to the above drawings, it should not be so construed to be so limited. It would be obvious for those who possess ordinary skill in the art to make changes and modifications to this device without departing from the scope of the invention. Additionally, while the present invention has particular utility in measuring transient reflectance values, the invention is not so limited, but may also be used to measure all specular reflectance values.

What is claimed is:

1. A reflectometer comprising:
   radiation source;
   fixed detector for determining reflectance;
   rotating sample wheel containing an aperture and a sample cell, said sample wheel disposed in the optical path of said radiation source;
   rotating optical wheel having an axis of rotation transverse to the axis of rotation of said sample wheel, said optical wheel means disposed in the optical path of said radiation source;
   mirror means mounted upon said optical wheel for receiving radiation reflected from said sample cell and directing said reflected radiation into said detector, and for receiving radiation passing through said aperture and directing said unreflected radiation into said detector;
   drive motor; and
   drive means connected to said motor, said sample wheel and said optical wheel for simultaneously rotating both said sample wheel and said optical wheel.

2. A reflectometer according to claim 1 wherein said radiation source is fixed.

3. A reflectometer according to claim 1 wherein said drive means contains a pair of bevel gears for rotating said sample wheel and a pair of meshed tooth gears for rotating said optical wheel.

4. A reflectometer according to claim 3 wherein said bevel gears and said tooth gears are in a one-to-one ratio.

5. A reflectometer according to claim 1 wherein said mirror means are two reflecting mirrors.

6. A reflectometer according to claim 5 further including translation means attached to one of said reflecting mirrors, allowing said reflecting mirrors to translate perpendicularly to the axis of rotation of said optical wheel.

7. A reflectometer according to claim 5 further including a pivoting arm upon which said light source is located.

* * * * *